United States Patent
Lo et al.

(10) Patent No.: US 10,188,332 B2
(45) Date of Patent: Jan. 29, 2019

(54) METHOD AND SYSTEM FOR SENSING GLUCOSE CONCENTRATION

(71) Applicant: NATIONAL CHENG KUNG UNIVERSITY, Tainan (TW)

(72) Inventors: Yu-Lung Lo, Tainan (TW); Quoc-Hung Phan, Tainan (TW); Chia-Chi Liao, Taichung (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 0 days.

(21) Appl. No.: 15/862,611

(22) Filed: Jan. 4, 2018

(65) Prior Publication Data
US 2018/0228415 A1 Aug. 16, 2018

(30) Foreign Application Priority Data

Feb. 16, 2017 (TW) .............................. 106105137 A

(51) Int. Cl.
*G01J 4/00* (2006.01)
*A61B 5/1455* (2006.01)
(Continued)

(52) U.S. Cl.
CPC .......... *A61B 5/14558* (2013.01); *A61B 3/102* (2013.01); *A61B 5/0066* (2013.01);
(Continued)

(58) Field of Classification Search
CPC ... A61B 5/14558; A61B 3/102; A61B 5/0066; A61B 5/14532
(Continued)

(56) References Cited

U.S. PATENT DOCUMENTS

| 5,383,452 A * | 1/1995 | Buchert ............. A61B 5/14558 600/347 |
| 5,553,616 A * | 9/1996 | Ham .................. A61B 5/14558 128/925 |

(Continued)

FOREIGN PATENT DOCUMENTS

| CN | 102539119 A | 7/2012 |
| TW | 200928348 A | 7/2009 |

(Continued)

OTHER PUBLICATIONS

R. M. A. Azzam, "Propagation of partially polarized light through anisotropic media with or without depolarization: A differential 4×4 matrix calculus," J. Opt. Soc. Am., vol. 68, No. 12, pp. 1756-1767, Dec. 1978.

(Continued)

*Primary Examiner* — Roy M Punnoose
(74) *Attorney, Agent, or Firm* — CKC & Partners Co., Ltd.

(57) ABSTRACT

A system for sensing glucose concentration is provided and includes following components. A light source generates a light beam. The system may include a polarization state generator (PSG) for changing the polarization of the light beam, and then the light beam is emitted to a biological tissue. A polarization state analyzer (PSA) receives the light beam reflected from the biological tissue, and the received light beam is used to calculate Stokes vectors. A Mueller matrix is calculated according to the Stokes vectors. In some embodiments, the system includes an optical coherence tomography (OCT) in which the light beam is sensed by a detector for calculating the Mueller matrix. An optical rotation angle and a depolarization index are calculated in accordance with the differential Mueller matrix formalism.

(Continued)

The glucose concentration is calculated in accordance with the optical rotation angle and the depolarization index.

17 Claims, 8 Drawing Sheets

(51) Int. Cl.
*A61B 5/145* (2006.01)
*A61B 5/00* (2006.01)
*G01J 3/447* (2006.01)
*A61B 3/10* (2006.01)

(52) U.S. Cl.
CPC ........ *A61B 5/14532* (2013.01); *A61B 5/7235* (2013.01); *G01J 3/447* (2013.01)

(58) Field of Classification Search
USPC ........................................................ 356/364
See application file for complete search history.

(56) References Cited

U.S. PATENT DOCUMENTS

| | | | | |
|---|---|---|---|---|
| 5,687,721 | A * | 11/1997 | Kuhls | A61B 5/14558 356/364 |
| 5,871,442 | A * | 2/1999 | Madarasz | A61B 5/14558 356/364 |
| 5,920,393 | A * | 7/1999 | Kaplan | G01N 21/21 356/364 |
| 6,070,093 | A * | 5/2000 | Oosta | A61B 5/0095 356/39 |
| 6,591,121 | B1 * | 7/2003 | Madarasz | A61B 5/14558 356/364 |
| 6,636,752 | B1 * | 10/2003 | Madarasz | A61B 5/14558 356/364 |
| 7,245,952 | B2 | 7/2007 | Cameron | |
| 2004/0036854 | A1 * | 2/2004 | Fukuda | A61B 5/14558 356/39 |
| 2010/0234704 | A1 | 9/2010 | Cameron | |
| 2011/0184260 | A1 | 7/2011 | Robinson et al. | |

FOREIGN PATENT DOCUMENTS

| | | |
|---|---|---|
| TW | 201235655 A | 9/2012 |
| WO | 9734521 A1 | 9/1997 |

OTHER PUBLICATIONS

C. C. Liao et al., "Extraction of linear anisotropic parameters using optical coherence tomography and hybrid Mueller matrix formalism," Optics Express, vol. 23, No. 8, pp. 10653-10667, Apr. 20, 2015.

R. A. Chipman, "Depolarization index and the average degree of polarization," Applied Optics, vol. 44, No. 13, pp. 2490-2495, May 1, 2005.

B. J. DeBoo et al., "Depolarization of diffusely reflecting man-made objects," Applied Optics, vol. 44, No. 26, pp. 5434-5445, Sep. 10, 2005.

H. H. Lin et al., "Characterization of voltage-driven twisted nematic liquid crystal cell by dynamic polarization scanning ellipsometry," Optics Express, vol. 23, No. 8, p. 10213-10223, Apr. 20, 2015.

Thi-Thu-Hien Pham et al., "Extraction of effective parameters of turbid media utilizing the Mueller matrix approach: study of glucose sensing," Journal of Biomedical Optics, vol. 17, Issue 9, Sep. 2012.

Chia-Chi Liao et al., "Measurement of Multiple Optical Parameters of Birefrigent Sample Using Polarization-Sensitive Optical Coherence Tomography," Journal of Lightwave Technology, vol. 27, No. 5, pp. 483-493, Mar. 1, 2009.

Rafat R. Ansari et al., "New optical scheme for a polarimetric-based glucose sensor," Journal of Biomedical Optics, vol. 9, No. 1, pp. 103-115, Jan./Feb. 2004.

Chia-Chi Liao et al., "Extraction of anisotropic parameters of turbid media using hybrid model comprising differential- and decomposition-based Mueller matrices," Optics Express, vol. 21, No. 14, pp. 16831-16853, Jul. 15, 2013.

\* cited by examiner

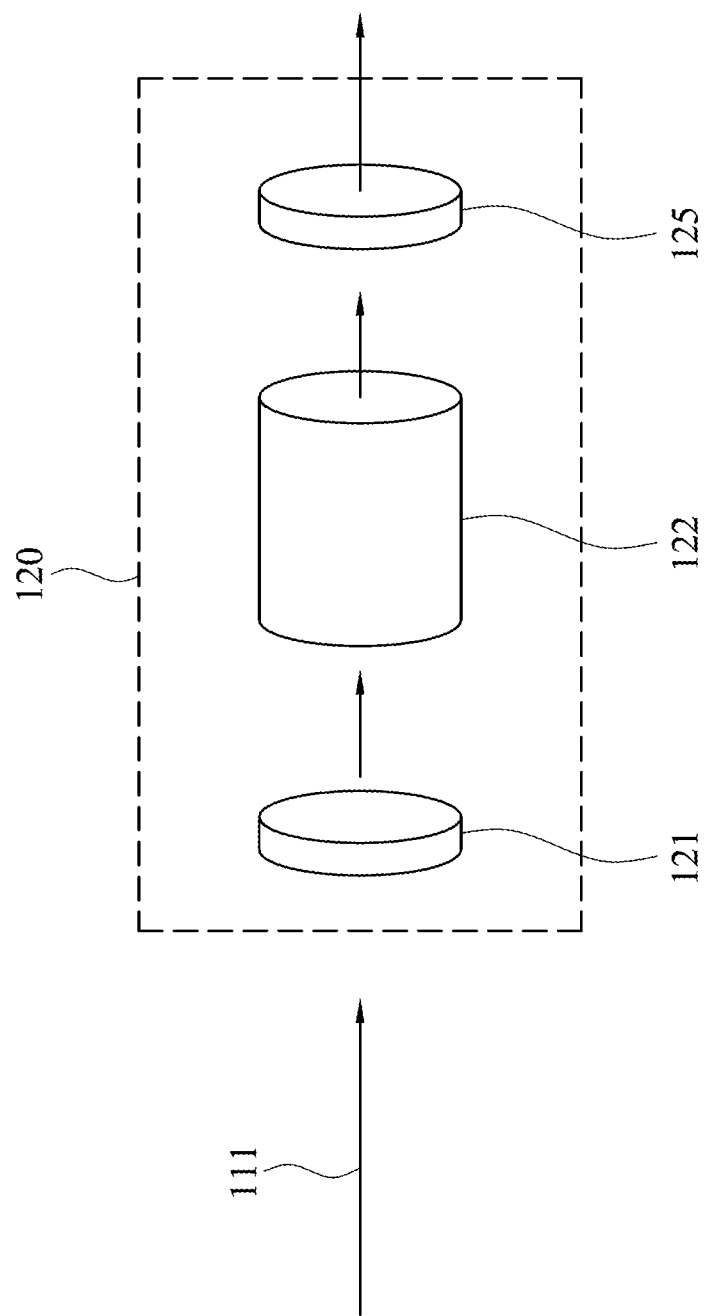

METHOD AND SYSTEM FOR SENSING GLUCOSE CONCENTRATION

RELATED APPLICATIONS

This application claims priority to Taiwan Application Serial Number 106105137 filed Feb. 16, 2017, which is herein incorporated by reference.

BACKGROUND

Field of Invention

The present invention relates to a non-invasive system for sensing a glucose concentration.

Description of Related Art

A polarization is a basic property of light and has many applications in the industrial or academic fields. In general, the polarization of a light beam can be represented by four Stokes parameters. When the light beam is emitted to an object, the optical property of the object can be represented by a Mueller matrix. Therefore, the mechanism of the Stokes-Mueller matrix can be used to identify many materials or biomaterials. On the other hands, it is an issue in the art about how to measure a glucose concentration of a biological tissue quickly and accurately.

SUMMARY

The system and method provided in the embodiments of the present invention can be applied to a non-invasive measurement and are capable of measuring a low glucose concentration (e.g. 20 mg/dl).

Embodiments of the invention provide a system for sensing glucose concentration. The system includes a light source, a polarization state generator, a polarization state analyzer, and a controlling module. The light source is configured to generate a light beam. The polarization state generator is configured to receive the light beam. The polarization state generator includes a modulator for changing a polarization of the light beam, and the light beam passing the modulator is emitted to a biological tissue. The polarization state analyzer is configured to receive the light beam reflected by the biological tissue. The controlling module is configured to transmit an electrical signal to the modulator. The electrical signal has n sampling points which correspond to n polarizations of the light beam respectively. The n polarizations are different from each other, and n is a positive integer greater than or equal to 4. For each of the n sampling points, the controlling module calculates a Stokes vector according to the light beam received by the polarization state analyzer. The controlling module calculates a Mueller matrix according to the Stokes vectors corresponding to the n sampling points, and calculates at least one parameter according to the Mueller matrix. The at least one parameter includes a depolarization index and an optical rotation angle. The controlling module calculates a glucose concentration corresponding to the biological tissue according to the at least one parameter.

In some embodiments, the polarization state generator further includes a polarizer disposed between the modulator and the light source, and a quarter-wave plate disposed between the modulator and the biological tissue. A principal axis of the polarizer is 0°. A principal axis of the quarter-wave plate is 0°. A principal axis of the modulator is 45°.

In some embodiments, the polarization state generator further includes a polarizer disposed between the modulator and the light source, a quarter-wave plate disposed between the modulator and the biological tissue; and a half-wave plate disposed between the quarter-wave plate and the biological tissue.

In some embodiments, the modulator is an electro-optic modulator. A principal axis of the polarizer is 0°. A principal axis of the electro-optic modulator is 45°. A principal axis of the quarter-wave plate is 45°, and a principal axis of the half-wave plate is 45°. A Stokes vector of the light beam emitted by the polarization state generator is represented by following equations (1) and (2):

$$S' = \begin{bmatrix} 1 \\ \cos a \\ \sin a \\ 1 \end{bmatrix} \quad (1)$$

$$a = \frac{\pi V}{V_{\lambda/2}} \quad (2)$$

S' is the Stokes vector of the light beam emitted by the polarization state generator, V is a constant, and $V_{\lambda/2}$ is an amplitude of the electrical signal.

In some embodiments, the polarization state analyzer includes a second electro-optic modulator with a principal axis of 0°, a third electro-optic modulator with a principal axis of 45°, an analyzer with a principal axis of 0°, and a detector. The second electro-optic modulator is disposed between the biological tissue and the third electro-optic modulator. The analyzer is disposed between the third electro-optic modulator and the detector, and the detector is configured to receive the light beam passing through the second electro-optic modulator, the third electro-optic modulator, and the analyzer.

In some embodiments, the controlling module performs a Fourier transform on brightness of the light beam received by the detector to obtain a plurality of brightness parameters, and calculates a plurality of Stokes parameters of the corresponding Stokes vector according to the plurality of brightness parameters.

In some embodiments, the controlling module calculates a differential Mueller matrix according to following equations (3) and (4).

$$\lambda_m = \ln(\lambda_M)/z \quad (3)$$

$$m = V_M m_\lambda V_M^{-1} = \begin{bmatrix} m_{11} & m_{12} & m_{13} & m_{14} \\ m_{21} & m_{22} & m_{23} & m_{24} \\ m_{31} & m_{32} & m_{33} & m_{34} \\ m_{41} & m_{42} & m_{43} & m_{44} \end{bmatrix} \quad (4)$$

z represents a direction that the light beam propagates along, m is the differential Mueller matrix, $V_M$ represents eigenvectors of the Mueller matrix, $\lambda_M$ represents eigenvalues of the Mueller matrix, $\lambda_m$ represents eigenvalues of the differential Mueller matrix, $m_\lambda$ is a diagonal matrix constituted by the eigenvalues $\lambda_m$, and the optical rotation angle is $\gamma=(m_{23}-m_{32})/4$.

In some embodiments, the controlling module generates a differential Mueller matrix $m_\Delta$ as the following equation (5) according to the differential Mueller matrix m.

$$m_\Delta = \begin{bmatrix} 0 & \frac{(m_{12}-m_{21})}{2} & \frac{(m_{13}-m_{31})}{2} & \frac{(m_{14}-m_{41})}{2} \\ \frac{(m_{21}-m_{12})}{2} & m_{22}-m_{11} & \frac{(m_{23}+m_{32})}{2} & \frac{(m_{24}+m_{42})}{2} \\ \frac{(m_{31}-m_{13})}{2} & \frac{(m_{23}+m_{32})}{2} & m_{33}-m_{11} & \frac{(m_{34}+m_{43})}{2} \\ \frac{(m_{41}-m_{14})}{2} & \frac{(m_{24}+m_{42})}{2} & \frac{(m_{34}+m_{43})}{2} & m_{44}-m_{11} \end{bmatrix} \quad (5)$$

The controlling module substitutes the differential Mueller matrix $m_\Delta$ into the equation (4) to calculate a Mueller matrix $M_\Delta$ as the following equation (6).

$$M_\Delta = \begin{bmatrix} 1 & K_{12} & K_{13} & K_{14} \\ -K_{12} & K_{22} & K_{23} & K_{24} \\ -K_{13} & K_{23} & K_{33} & K_{43} \\ -K_{14} & K_{24} & K_{34} & K_{44} \end{bmatrix} \quad (6)$$

The depolarization index is represented as the following equation (7).

$$\Delta = 1 - \sqrt{\frac{K_{22}^2 + K_{33}^2 + K_{44}^2}{3}} \quad (7)$$

In some embodiments, the controlling module substitutes the parameter γ into a linearly increasing function to obtain the glucose concentration, or substitutes the parameter Δ into a linearly decreasing function to obtain the glucose concentration.

From another aspect, embodiments of the invention provide a method for sensing glucose concentration for a system which includes a light source, a polarization state generator, and a polarization state analyzer. A light beam generated by the light source is emitted to the polarization state generator and then is emitted to a biological tissue, and the polarization state analyzer receives the light beam reflected by the biological tissue. The method includes: transmitting an electrical signal to a modulator of the polarization state generator, in which the electrical signal has n sampling points which correspond to n polarizations of the light beam respectively, the n polarizations are different from each other, and n is a positive integer greater than or equal to 4; calculating a Stokes vector according to the light beam received by the polarization state analyzer for each of the n sampling point; and calculating a Mueller matrix according to the Stokes vectors corresponding to the n sampling points, calculating at least one parameter according to the Mueller matrix, and calculating a glucose concentration corresponding to the biological tissue according to the at least one parameter.

From another aspect, embodiments of the invention provide a system for sensing glucose concentration. The system includes a light source configured to generate a light beam; and an optical coherence tomography (OCT) device for receiving the light beam. The OCT device has at least one detector. A controlling module calculates a Muller matrix according to signals received by the at least one detector, and calculates an optical rotation angle and a depolarization index according to the Muller matrix, and calculates a glucose concentration corresponding to a sample according to the optical rotation angle and the depolarization index.

In some embodiments, the OCT device includes the optical coherence tomography device comprises: a polarization state generator for receiving the light beam and change a polarization of the light beam; a first detecting module for compensating the light beam; a second detecting module coupled to the first detecting module; a reference arm disposed at a side of the second detecting module; and a measurement arm, disposed at another side of the second detecting module.

In some embodiments, the OCT device includes the following components. A polarizer and a quarter-wave plate are configured to receive light. A first non-polarizing beam splitter (NPBS) has a first side, a second side, a third side and a fourth side, in which the first side is opposite to the third side, and the second side is opposite to the fourth side. The polarizer and the quarter-wave plater are disposed at the first side of the first NPBS. A first mirror is disposed at the second side of the first NPBS. A first detector is disposed at the fourth side of the first NPBS. A second NPBS is disposed at the third side of the first NPBS and has a first side, a second side, a third side and a fourth side, in which the first side is opposite to the third side, and the second side is opposite to the fourth side. A second mirror is disposed at the second side of the second NPBS. A variable wave plater is disposed between the second mirror and the second NPBS. A third mirror is disposed at the third side of the second NPBS. The sample is disposed between the third mirror and the second NPBS. A second detector is disposed at the fourth side of the second NPBS.

In some embodiments, the controlling module rotates the quarter-wave plate and the polarizer, and adjusts the variable wave plate to produce at least 16 interferometric signals detected by the second detector. The controlling module calculates the Muller matrix according to the 16 interferometric signals.

In some embodiments, the controlling module obtains an optical path length in accordance with the following equation (8):

$$\Delta = e^{-L/l} \quad (8)$$

where Δ is the depolarization index, L is a length of the sample, and l is the optical path length. The controlling module calculates the glucose concentration corresponding to the sample in accordance with the following equation (9):

$$C = \frac{\gamma}{[\gamma]_T^\lambda l} \quad (9)$$

where C is the glucose concentration, γ is the optical rotation angle, $[\gamma]_T^\lambda$; is the optical rotation angle of the sample at room temperature T, and λ is a wavelength of the light beam.

BRIEF DESCRIPTION OF THE DRAWINGS

The invention can be more fully understood by reading the following detailed description of the embodiment, with reference made to the accompanying drawings as follows.

FIG. 3 is a schematic diagram of a polarization state generator for generating linear polarization in accordance with an embodiment.

DETAILED DESCRIPTION

Specific embodiments of the present invention are further described in detail below with reference to the accompanying drawings, however, the embodiments described are not intended to limit the present invention and it is not intended for the description of operation to limit the order of implementation. Moreover, any device with equivalent functions that is produced from a structure formed by a recombination of elements shall fall within the scope of the present invention. Additionally, the drawings are only illustrative and are not drawn to actual size.

The using of "first", "second", "third", etc. in the specification should be understood for identifying units or data described by the same terminology, but are not referred to particular order or sequence.

Figure 1:
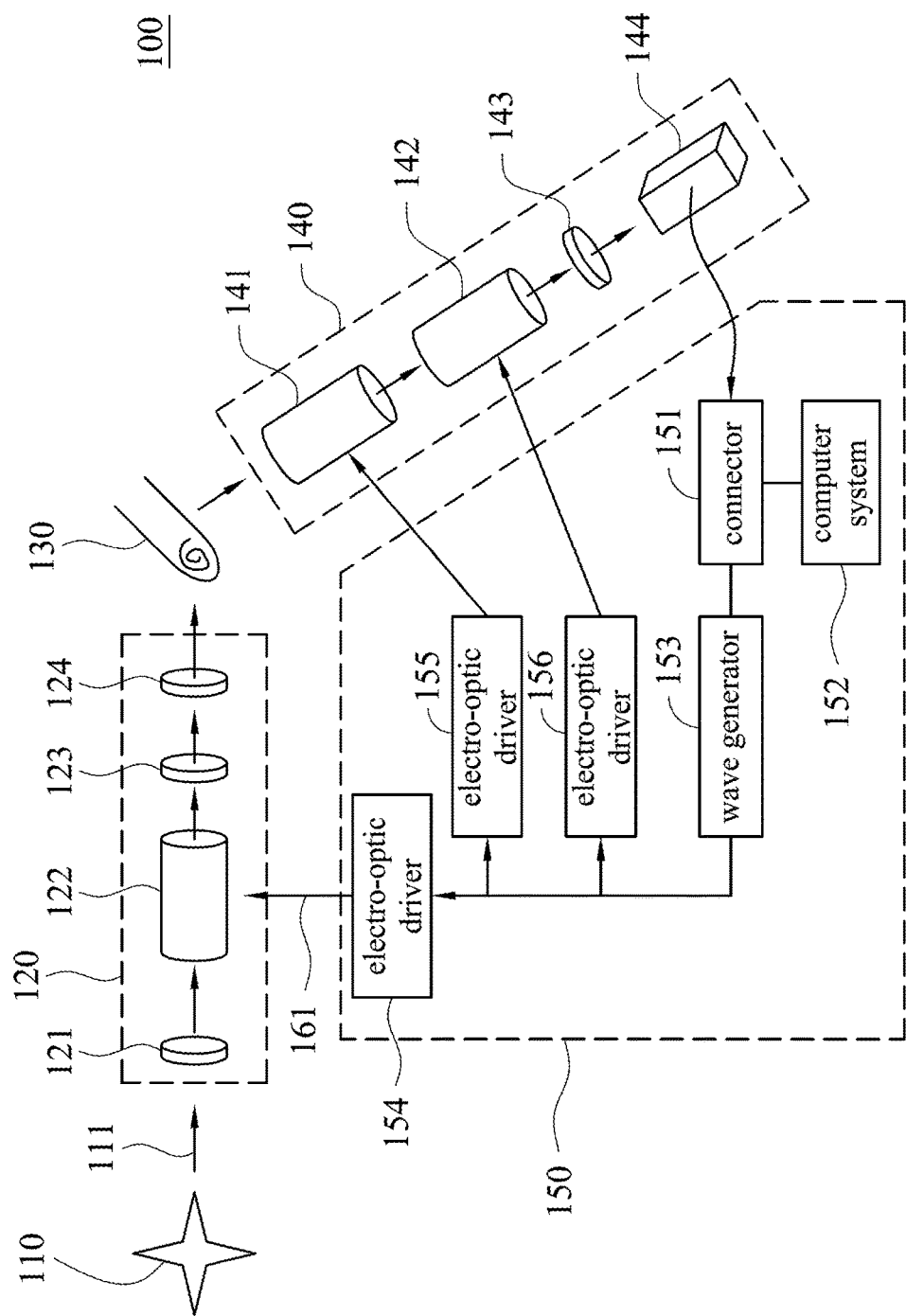
FIG. 1 is a schematic diagram of a non-invasive system for sensing glucose concentration in accordance with an embodiment.

FIG. 1 is a schematic diagram of a non-invasive system for sensing a glucose concentration in accordance with an embodiment. Referring to FIG. 1, a sensing system 100 includes a light source 110, a polarization state generator (PSG) 120, a polarization state analyzer (PSA) 140 and a controlling module 150. In some embodiments, the sensing system 100 is a portable device, in which one or more components are integrated into a single device, but the shape and the size of the sensing system 100 are not limited in the invention.

The light source 110 emits a light beam 111. The light source 110 is, for example, a laser light source or a broadband light source. The type and the frequency of the light beam 111 are not limited in the invention. In some embodiments, the light source 110 is a He—Ne laser.

The polarization state generator 120 receives the light beam 111, and changes the polarization of the light beam 111. For example, the polarization state generator 120 includes a polarizer 121, an electro-optic modulator (EO) 122, a quarter-wave plate 123 and a half-wave plate 124. In the embodiment, the polarizer 121 is disposed between the light source 110 and the electro-optic modulator 122, the quarter-wave plate 123 is disposed between the electro-optic modulator 122 and the biological tissue 130, and the half-wave plate 124 is disposed between the quarter-wave plate 123 and the biological tissue 130. In other words, after the light beam 111 passes through the polarizer 121, the electro-optic modulator 122, the quarter-wave plate 123 and the half-wave plate 124 sequentially, it is emitted to a biological tissue 130.

In some embodiments, the biological tissue 130 is a human finger. After the light beam is emitted to the biological tissue, it is reflected to the polarization state generator 140. However, the biological tissue 130 may be any organ or any body part of any animal (including human) in other embodiments. Alternatively, the biological tissue 130 may be blood or other tissues on a carrier or in a container, which is not limited in the invention.

The polarization state analyzer 140 receives the light beam reflected from the biological tissue 130. For example, the polarization state analyzer 140 includes an electro-optic modulator 141 (also referred to as a second electro-optic modulator), an electro-optic modulator 142 (also referred to as a third electro-optic modulator), an analyzer 143 and a detector 144. The electro-optic modulator 141 is disposed between the biological tissue 130 and the electro-optic modulator 142, and the analyzer 143 is disposed between the electro-optic modulator 142 and the detector 144. That is to say, the detector 144 receives the light beam which passes through the electro-optic modulator 141, the electro-optic modulator 142 and the analyzer 143.

The controlling module 150 controls the electro-optic modulators 122, 141, and 142, and receives signals from the detector 144 for calculating a glucose concentration corresponding to the biological tissue 130. In some embodiments, the controlling module 150 includes a connector 151, a computer system 152, a wave generator 153 and electro-optic drivers 154-156. The connector 151 is coupled to the detector 144, the computer system 152 and the wave generator 153. The computer system 152 receives signals from the detector 144 through the connector 151, and transmits instructions/signals to the wave generator 153 through the connector 151. The wave generator 153 controls the electro-optic drivers 154-156 to generate corresponding electrical signals for the electro-optic modulators 122, 141, and 142. However, the invention is not limited thereto, and the controlling module 150 may be implemented as hardware, software, or the combination thereof.

The electro-optic modulators are used to change the polarization of the light beam in the aforementioned embodiments. However, other types of modulators may be used in other embodiments. For example, one or multiple of the electro-optic modulators 122, 141, and 142 may be replaced with magnetic modulators, pressure modulators, or any other suitable type of modulators.

Figure 2:
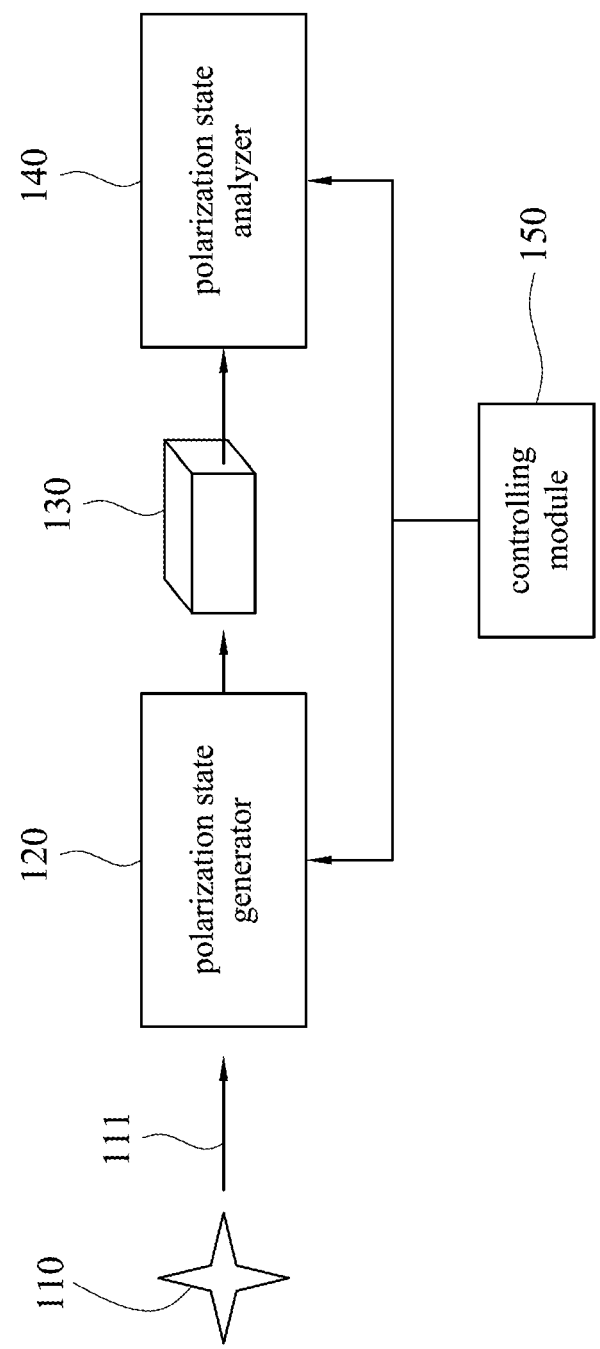
FIG. 2 is a system for receiving a light beam passing through a biological tissue in accordance with an embodiment.

In FIG. 1, the sensing system 100 is non-invasive for sensing the light beam reflected from the biological tissue 130, but the system may sense the light beam passing through the biological tissue 130 in other embodiments. For example, referring to FIG. 2, the components of FIG. 2 that are similar to the components of FIG. 1 are not described again. In FIG. 2, after the light beam 111 passes through the polarization state generator 120, it is emitted to the biological tissue 130 and penetrates the biological tissue 130. The polarization state analyzer 140 would receive the light beam penetrating the biological tissue 130. However, no matter the reflected light beam or the penetrating light beam is sensed, the calculation of glucose concentration described in the following paragraphs would not be affected.

The calculation of the glucose concentration is described herein. Stokes vector and Mueller matrix have to be described first. One Stokes vector has four parameters generally represented as $S_0$, $S_1$, $S_2$, and $S_3$. The parameter $S_0$ indicates the sum of the power of the electric fields of the light beam (i.e. a type of electromagnetic wave) along two orthogonal directions. The parameter $S_1$ indicates the difference of the power of the electric fields along the two orthogonal directions. The parameters $S_2$, $S_3$ are used to provide information of the polarization angle and the state of the circular polarization. The person in the art should be able to understand the definition of Stokes vector, and therefore it will not be described in detail.

A general optical sampling is represented as $S_{out}=M \times S_{in}$, where $S_{in}$ is the Stokes vector of the light beam emitted to the biological tissue, and $S_{out}$ is the Stokes vectors of the light beam reflected or penetrating from the biological tissue. The optical properties of the biological tissue can be represented as a Mueller matrix M (also referred to as a macroscopic Mueller matrix) as the following equation (1).

$$S_{out} = \begin{bmatrix} M_{11} & M_{12} & M_{13} & M_{14} \\ M_{21} & M_{22} & M_{23} & M_{24} \\ M_{31} & M_{32} & M_{33} & M_{34} \\ M_{41} & M_{42} & M_{43} & M_{44} \end{bmatrix} \times S_{in} \tag{1}$$

The Mueller matrix M may be transformed into one or more differential Mueller matrices to describing different optical properties. It is assumed that the light beam propagates along the z-axis of a right-handed Cartesian coordinate system. The differential Mueller matrix is thus given by the following equation (2).

$$m = (dM/dz)M^{-1} \tag{2}$$

m represents the differential Mueller matrix. The eigenvectors of the Mueller matrix M and the differential Mueller matrix m are represented as $V_M$ and $V_m$, respectively. The eigenvalues of the Mueller matrix M and the differential Mueller matrix m are represented as $\lambda_M$ and $\lambda_m$, respectively. Assume that the initial condition matrix Mueller matrix $M_{Z=0}$ has the form of an identity matrix. The eigenvalues $\lambda_M$ and $\lambda_m$ are related as the following equation (3), and thus the eigenvalues $\Delta_m$ can be calculated after the eigenvalues $\lambda_M$ are obtained.

$$\lambda_m = ln(\lambda_M)/Z \tag{3}$$

Assuming that $m_\lambda$ is a diagonal matrix with diagonal elements of eigenvalues $\lambda_m$, the differential Mueller matrix m can be obtained from an eigen analysis of the Mueller matrix M as the following equation (4).

$$m = V_M m_\lambda V_M^{-1} = \begin{bmatrix} m_{11} & m_{12} & m_{13} & m_{14} \\ m_{21} & m_{22} & m_{23} & m_{24} \\ m_{31} & m_{32} & m_{33} & m_{34} \\ m_{41} & m_{42} & m_{43} & m_{44} \end{bmatrix} \tag{4}$$

In accordance with the analysis of the differential Mueller matrix, a general anisotropic sample can be partitioned into 16 different elements, with each element describing a different aspect of the basic optical behavior. Let $M_{LB}$, $M_{CB}$, $M_{LD}$, and $M_{CD}$ be the macroscopic Mueller matrices describing the linear birefringence (LB), circular birefringence (CB), linear dichroism (LD) and circular dichroism (CD) properties. A differential matrix $m_{BD}$ of a composite sample with LB, CB, LD, and CD optical properties can be expressed as the following equation (5).

$$m_{BD} = \frac{1}{d}\begin{bmatrix} \ln\left[(1-R^2)\sqrt{\frac{1-D}{1+D}}\right] & -\ln\sqrt{\frac{1-D}{1+D}}\cos(2\theta_d) & -\ln\sqrt{\frac{1-D}{1+D}}\sin(2\theta_d) & \ln\left(\frac{1+R}{1-R}\right) \\ -\ln\sqrt{\frac{1-D}{1+D}}\cos(2\theta_d) & \ln\left[(1-R^2)\sqrt{\frac{1-D}{1+D}}\right] & 2\gamma & -\beta\sin(2\alpha) \\ -\ln\sqrt{\frac{1-D}{1+D}}\sin(2\theta_d) & -2\gamma & \ln\left[(1-R^2)\sqrt{\frac{1-D}{1+D}}\right] & \beta\cos(2\alpha) \\ \ln\left(\frac{1+R}{1-R}\right) & \beta\sin(2\alpha) & -\beta\cos(2\alpha) & \ln\left[(1-R^2)\sqrt{\frac{1-D}{1+D}}\right] \end{bmatrix} \tag{5}$$

In the equation (5), d is the sample thickness; $\alpha$ and $\mu$ are the orientation angle and phase retardation of the LB property, respectively; $\gamma$ is the optical rotation angle of the CB property; $\theta_d$ and D are the orientation angle and linear dichroism of the LD property, respectively; and R is the circular amplitude anisotropy of the CD property (i.e. $R=(r_R-r_L)/(r_R+r_L)$, $-1 \leq R \leq +1$, were $r_R$ and $r_L$ are the absorptions of right-hand circular polarized light and left-hand circular polarized light, respectively).

The differential Mueller matrix describing the depolarization effect in depolarizing anisotropic media is expressed as the following equation (6).

$$m_\Delta = \frac{1}{d}\begin{bmatrix} 0 & \kappa'_q & \kappa'_u & \kappa'_v \\ -\kappa'_q & -\kappa'_{iq} & \eta'_v & \eta'_u \\ -\kappa'_u & \eta'_v & -\kappa'_{iu} & \eta'_q \\ -\kappa'_v & \eta'_u & \eta'_q & -\kappa'_{iv} \end{bmatrix} \tag{6}$$

The diagonal depolarization is characterized by the parameters $K_{iq}'$, $K_{iu}'$, and $K_{iv}'$. The anomalous dichroism and anomalous depolarization are characterized by the parameters $K_{q,u,v}'$, and $\eta_{q,u,v}'$.

The differential Mueller matrix describing all of the LB, CB, LD, CD and Dep properties of an anisotropic optical sample can be obtained by summing equations (5), and (6) as the following equation (7).

$$m_{BD\Delta} = m_{BD} + m_\Delta = \frac{1}{d}\begin{bmatrix} \ln\left[(1-R^2)\sqrt{\frac{1-D}{1+D}}\right] & -\ln\sqrt{\frac{1-D}{1+D}}\cos(2\theta_d) + k'_q & -\ln\sqrt{\frac{1-D}{1+D}}\sin(2\theta_d) + k'_u & \ln\left(\frac{1+R}{1-R}\right) + k'_v \\ -\ln\sqrt{\frac{1-D}{1+D}}\cos(2\theta_d) - k'_q & \ln\left[(1-R^2)\sqrt{\frac{1-D}{1+D}}\right] - k'_{iq} & 2\gamma + \eta'_v & -\beta\sin(2\alpha) + \eta'_u \\ -\ln\sqrt{\frac{1-D}{1+D}}\sin(2\theta_d) - k'_u & -2\gamma + \eta'_v & \ln\left[(1-R^2)\sqrt{\frac{1-D}{1+D}}\right] - k'_{iu} & \beta\cos(2\alpha) + \eta'_q \\ \ln\left(\frac{1+R}{1-R}\right) - k'_v & \beta\sin(2\alpha) + \eta'_u & -\beta\cos(2\alpha) + \eta'_q & \ln\left[(1-R^2)\sqrt{\frac{1-D}{1+D}}\right] - k'_{iv} \end{bmatrix} \quad (7)$$

In operation, the macroscopic Mueller matrix M can be determined from the equation (1), and the differential Mueller matrix can be calculated by using the equation (4). The optical parameters describing the anisotropic behavior of the sample can be obtained by equating the differential Mueller matrix of the equation (4) with that of the equation (7). By doing so, the orientation angle $\alpha$, phase retardation $\beta$, optical rotation angle $\gamma$, orientation angle $\theta_d$, linear dichroism D and circular dichroism R can be obtained respectively as the following equations (8)-(13).

$$\alpha = \frac{1}{2}\tan^{-1}\left(\frac{m_{42} - m_{24}}{m_{34} - m_{43}}\right) \quad (8)$$

$$\beta = \sqrt{\left[\frac{(m_{42} - m_{24})}{2}\right]^2 + \left[\frac{(m_{34} - m_{43})}{2}\right]^2} \quad (9)$$

$$\gamma = \frac{(m_{23} - m_{32})}{4} \quad (10)$$

$$\theta_d = \frac{1}{2}\tan^{-1}\left(\frac{m_{13} + m_{31}}{m_{12} + m_{21}}\right) \quad (11)$$

$$D = \frac{1 - e^{-2\sqrt{(m_{12}+m_{21})^2 + (m_{13}+m_{31})^2}}}{1 + e^{-2\sqrt{(m_{12}+m_{21})^2 + (m_{13}+m_{31})^2}}} \quad (12)$$

$$R = \frac{e^{\left(\frac{m_{14}+m_{41}}{2}\right)} - 1}{e^{\left(\frac{m_{14}+m_{41}}{2}\right)} + 1} \quad (13)$$

Similarly, the differential Mueller matrix describing the depolarization effect can be obtained by the following equation (14).

$$m_\Delta = \begin{bmatrix} 0 & \frac{(m_{12}-m_{21})}{2} & \frac{(m_{13}-m_{31})}{2} & \frac{(m_{14}-m_{41})}{2} \\ \frac{(m_{21}-m_{12})}{2} & m_{22} - m_{11} & \frac{(m_{23}+m_{32})}{2} & \frac{(m_{24}+m_{42})}{2} \\ \frac{(m_{31}-m_{13})}{2} & \frac{(m_{23}+m_{32})}{2} & m_{33} - m_{11} & \frac{(m_{34}+m_{43})}{2} \\ \frac{(m_{41}-m_{14})}{2} & \frac{(m_{24}+m_{42})}{2} & \frac{(m_{43}+m_{43})}{2} & m_{44} - m_{11} \end{bmatrix} \quad (14)$$

By performing inverse differential calculation on the differential matrix $m_\Delta$ in accordance with the equation (4), a macroscopic Mueller matrix $M_\Delta$ is obtained as the following equation (15).

$$M_\Delta = \begin{bmatrix} 1 & K_{12} & K_{13} & K_{14} \\ -K_{12} & K_{22} & K_{23} & K_{24} \\ -K_{13} & K_{23} & K_{33} & K_{43} \\ -K_{14} & K_{24} & K_{34} & K_{44} \end{bmatrix} \quad (15)$$

$K_{22}$ and $K_{33}$ are degrees of linear depolarization, and $K_{44}$ is the degree or circular depolarization. In general, the degree of depolarization is quantified by a depolarization index $\Delta$. When the value of the depolarization index $\Delta$ is 0, it indicates a non-depolarizing sample; and when the value is 1, it indicates an ideal depolarizer. The depolarization index $\Delta$ is expressed as the following equation (16).

$$\Delta = 1 - \sqrt{\frac{K_{22}^2 + K_{33}^2 + K_{44}^2}{3}} \quad (16)$$

Referring to FIG. 1, the calculation of the Mueller matrix is described herein. In some embodiments, the principal axis of the polarizer 121 is 0°, the principal axis of the electro-optic modulator 122 is 45°, the principal axis of the quarter-wave plate 123 is 45°, and the principal axis of the half-wave plate 124 is 45°. In addition, the light beam emitted by the light source 110 is represented as the Stokes vector $S_{in}$, the light beam emitted by the polarization state generator 120 is represented as the Stokes vector S', and the relationship between these two vectors are expressed as the following equation (17).

$$S' = H(45°)Q(45°)EO(45°)P(0°)S_{in} \quad (17)$$

The equation (17) can be further expressed as the equation (18).

$$\begin{bmatrix} 1 \\ \cos a \\ \sin a \\ 1 \end{bmatrix} = \begin{bmatrix} 1 & 0 & 0 & 0 \\ 0 & 1 & 0 & 0 \\ 0 & 0 & -1 & 0 \\ 0 & 0 & 0 & -1 \end{bmatrix} \begin{bmatrix} 1 & 0 & 0 & 0 \\ 0 & 1 & 0 & 0 \\ 0 & 0 & 0 & -1 \\ 0 & 0 & 1 & 0 \end{bmatrix} \begin{bmatrix} 1 & 0 & 0 & 0 \\ 0 & \cos a & 0 & -\sin a \\ 0 & 0 & 1 & 0 \\ 0 & \sin a & 0 & \cos a \end{bmatrix} \begin{bmatrix} 1/2 & 1/2 & 0 & 0 \\ 1/2 & 1/2 & 0 & 0 \\ 0 & 0 & 0 & -1 \\ 0 & 0 & 1 & 0 \end{bmatrix} \begin{bmatrix} 1 \\ 1 \\ 0 \\ 0 \end{bmatrix} \quad (18)$$

In the equation (18), a is a parameter for adjusting phase retardation of the electro-optic modulator 122. The electro-optic driver 154 outputs an electrical signal 161 to the electro-optic modulator 122 for changing the parameter a. To be specific, the parameter a can be expressed as the following equation (19).

$$a = \frac{\pi V}{V_{\lambda/2}} \tag{19}$$

In the equation (19), V is a constant, and $V_{\lambda/2}$ is the amplitude of the electrical signal 161. In some embodiments, the electrical signal 161 is a periodic saw-tooth signal. However, the invention is not limited thereto, other forms of signals such as sine wave, cosine wave, square wave, or any other wave can be applied in other embodiments. Besides, the electrical signal 161 may be a non-periodic signal in other embodiments.

In the embodiment of FIG. 1, the polarization state generator 120 is used to generate the light beam with circular polarization. However, in other embodiments, the polarization state generator 120 may be used to generate the light beam with linear polarization. For example, referring to FIG. 3, the polarization state generator 120 includes a polarizer 121, an electro-optic modulator 122 and a quarter-wave plate 125. The principal axis of the polarizer 121 is 0°, the principal axis of the electro-optic modulator 122 is 45°, and the principal axis of the quarter-wave plate 125 is 45°. In the embodiment of FIG. 3, the relationship between the Stokes vector $S_{in}$ and the Stokes vector S' is expressed as the following equations (20) and (21).

$$S' = Q(0°)EO(45°)S_{in} \tag{20}$$

$$\begin{bmatrix} 1 \\ \cos a \\ \sin a \\ 0 \end{bmatrix} = \begin{bmatrix} 1 & 0 & 0 & 0 \\ 0 & 1 & 0 & 0 \\ 0 & 0 & 0 & 1 \\ 0 & 0 & -1 & 0 \end{bmatrix} \begin{bmatrix} 1 & 0 & 0 & 0 \\ 0 & \cos a & 0 & -\sin a \\ 0 & 0 & 1 & 0 \\ 0 & \sin a & 0 & \cos a \end{bmatrix} \begin{bmatrix} 1 \\ 1 \\ 0 \\ 0 \end{bmatrix} \tag{21}$$

Similarly, the electro-optic driver 154 outputs the electrical signal 161 to the electro-optic modulator 122 for changing the parameter a. The electro-optic modulator 122 is used to change the polarization of the light beam no matter circular polarization or the linear polarization is adopted. Since the light beam with a certain polarization has four Stokes parameters, and the Mueller matrix has 16 unknown variables, we need at least four polarizations of the light beam to determine the Mueller matrix. In the embodiment, one period of the electrical signal 161 has n sampling points which correspond to n different parameters a. In other words, the n sampling points correspond to n polarizations which are different from each other. In addition, n is a positive integer greater than or equal to 4. For example, the positive integer n may be equal to 200, which is not limited in the invention. In other embodiments, the positive integer n may be any integer greater than 50, 100 or 300.

The light beam with different polarizations is emitted to the biological tissue 130 and is received, after reflected or penetrating from the biological tissues 130, by the polarization state analyzer 140. In some embodiments, the principal axis of the electro-optic modulator 141 is 0°, the principal axis of the electro-optic modulator 142 is 45°, and the principal axis of the analyzer 143 is 0°. Therefore, the Stokes vector $S_{OUT}$ of the light beam received by the detector 144 is expressed by the following equation (22).

$$S_{OUT} = A(0°)EO(45°)EO(0°)S' \tag{22}$$

The equation (22) can be further expressed as the following equation (23).

$$\begin{bmatrix} I(\beta_1, \beta_2) \\ I(\beta_1, \beta_2) \\ 0 \\ 0 \end{bmatrix} = \begin{bmatrix} 1/2 & 1/2 & 0 & 0 \\ 1/2 & 1/2 & 0 & 0 \\ 0 & 0 & 0 & 0 \\ 0 & 0 & 0 & 0 \end{bmatrix} \cdot \begin{bmatrix} 1 & 0 & 0 & 0 \\ 0 & \cos \beta_2 & 0 & -\sin \beta_2 \\ 0 & 0 & 1 & 0 \\ 0 & \sin \beta_2 & 0 & \cos \beta_2 \end{bmatrix}$$

$$\begin{bmatrix} 1 & 0 & 0 & 0 \\ 0 & 1 & 0 & 0 \\ 0 & 0 & \cos \beta_1 & \sin \beta_1 \\ 0 & 0 & -\sin \beta_1 & \cos \beta_1 \end{bmatrix} \begin{bmatrix} S_0 \\ S_1 \\ S_2 \\ S_3 \end{bmatrix} \tag{23}$$

In the equation (23), $\beta_1$ and $\beta_2$ are parameters for adjusting phase retardation of the electro-optic modulators 141 and 142 respectively and they are controlled in accordance with the equation (19). In other words, the electro-optic drivers 155 and 156 transmit two electrical signals to the electro-optic modulators 141 and 142 respectively, and the amplitudes of these two electrical signals are the parameter $V_{\lambda/2}$ in the equation (19). Accordingly, the brightness of the light beam received by the detector 144 is expressed as the following equation (24).

$$I(\beta_1, \beta_2) = A + B \cos \beta_2 + C \sin \beta_1 \sin \beta_2 + D \cos \beta_1 \sin \beta_2 \tag{24}$$

If the parameters $\beta_1$ and $\beta_2$ are the same, then the equation (24) is written as the following equation (25).

$$I(\beta_1) = A + B \cos(\beta_1) + C \sin(2\beta_1) + D \sin(2\beta_1) \tag{25}$$

In the equation (25), $A = 0.5 S_0 - 0.25 S_2$, $B = 0.5 S_1$, $C = 0.25 S_2$, and $D = 0.25 S_3$. The controlling module 150 performs a Fourier transform on the light beam received by the detector 144 to obtain the brightness parameters A, B, C, and D, and calculates Stokes parameters of the corresponding Stokes vector based on these brightness parameters. In detail, the brightness parameters A, B, C, and D are obtained as the following equations (26)-(29) respectively.

$$A = \frac{1}{2\pi} \int_{\beta_{-\lambda/2}}^{\beta_{\lambda/2}} I(\beta_1).d(\beta_1) \tag{26}$$

$$B = \frac{1}{\pi} \int_{\beta_{-\lambda/2}}^{\beta_{\lambda/2}} I(\beta_1).\cos(\beta_1).d(\beta_1) \tag{27}$$

$$C = \frac{1}{\pi} \int_{\beta_{-\lambda/2}}^{\beta_{\lambda/2}} I(\beta_1).\cos(2\beta_1).d(\beta_1) \tag{28}$$

$$D = \frac{1}{\pi} \int_{\beta_{-\lambda/2}}^{\beta_{\lambda/2}} I(\beta_1).\sin(2\beta_1).d(\beta_1) \tag{29}$$

$\beta_{\lambda/2}$ is the induced half-wave retardation. Once the brightness parameters A, B, C, and D are known, the Stokes parameters $S_0$-$S_3$ can be obtained.

For each sampling point of the electrical signal, the controlling module calculates the corresponding Stokes vector according to the light beam received by the polarization state analyzer. In the embodiment, there are 200 Stokes vectors in one period. Therefore, the Mueller matrix M can be obtained in accordance with the equation (1), and the differential Mueller matrix m is calculated in accordance with the equations (3) and (4). After the differential Mueller matrix is obtained, the parameters such as the orientation angle α, the phase retardation β, the optical rotation angle γ, the orientation angle $\theta_d$, the linear dichroism D and the circular amplitude anisotropy R can be obtained in accordance with the equations (8)-(13). In some embodiments, there may not be a set of parameters α, β, γ, $\theta_d$, D, R causing that the equation (4) is perfectly matched with the equation (7). Therefore, some numerical methods may be adopted to find the set of parameters α, β, γ, $\theta_d$, D, R for minimizing the error between the equation (4) and the equation (7). For example, the root mean square error of all elements between the equation (4) and the equation (7) may be set as an objective function, and the parameters α, β, γ, $\theta_d$, D, R serve as a DNA to perform a genetic algorithm. However, how the parameters α, β, γ, $\theta_d$, D, R are found is not limited in the invention. On the other hand, the depolarization index Δ can be obtained in accordance with the equations (14)-(16). In the embodiment, the optical rotation angle γ and the depolarization index Δ are used to calculate the glucose concentration.

Figure 4A:
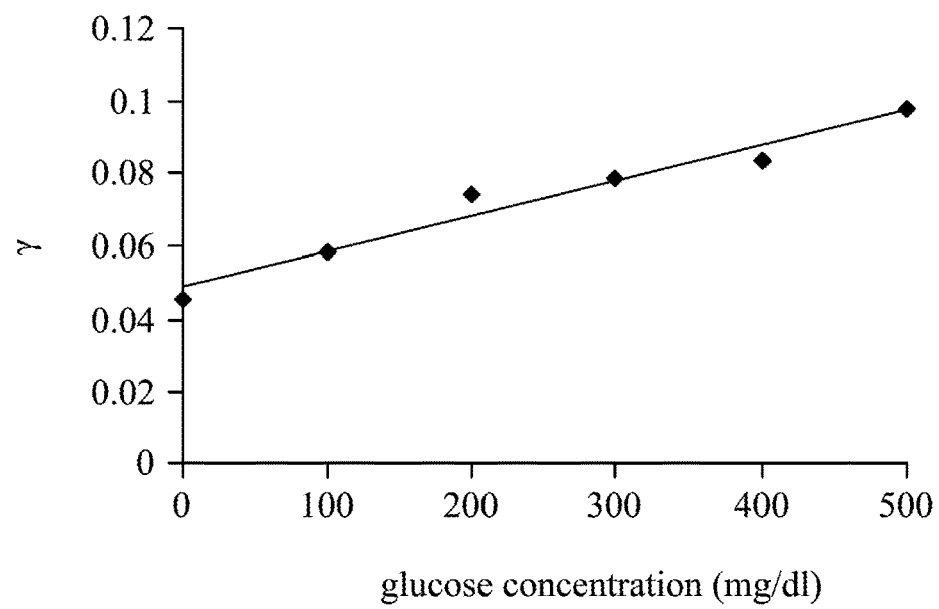
FIG. 4a, 4b, 5a, 5b are diagrams illustrating relationships between parameters and the glucose concentration in accordance with an embodiment.
Figure 4B:
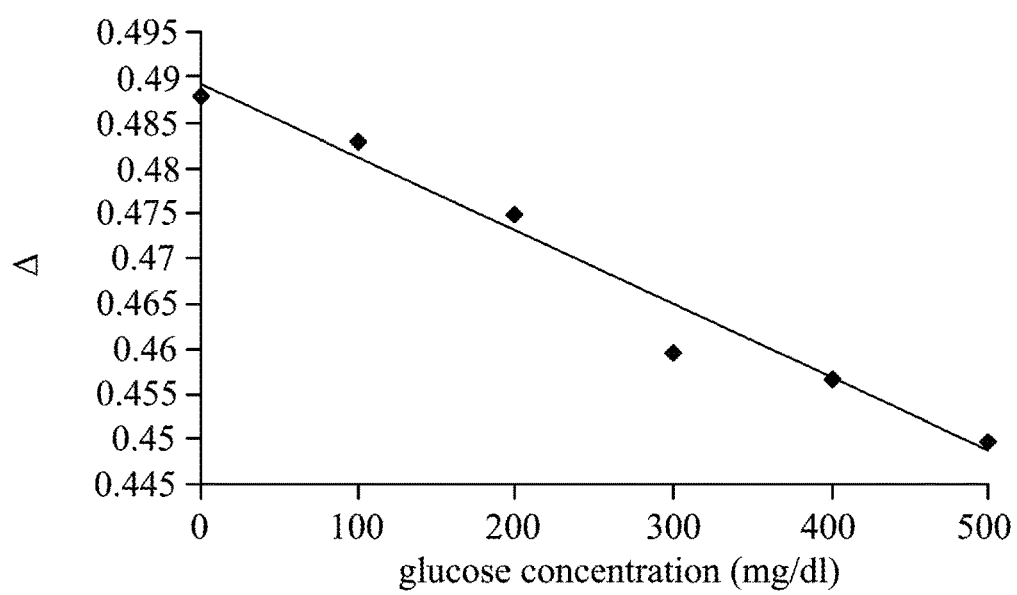
Figure 5A:
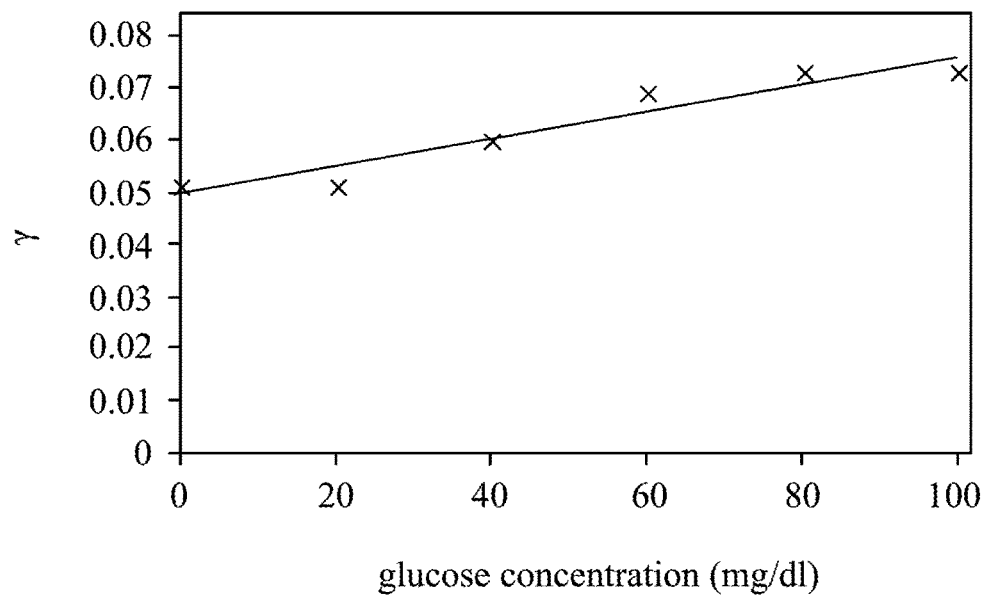
Figure 5B:
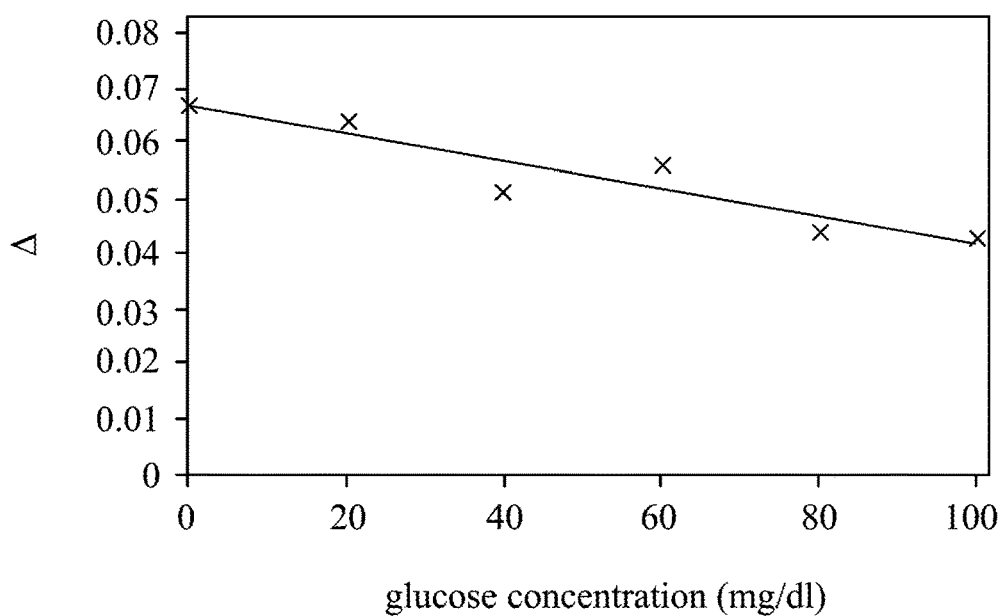

To be specific, FIG. 4a, 4b, 5a, 5b are diagrams illustrating relationships between parameters and the glucose concentration in accordance with an embodiment. FIG. 4a shows the relationship between the optical rotation angle γ and the glucose concentration, and the relationship is approximated as a linearly increasing function. FIG. 4b shows the relationship between the depolarization index Δ and the glucose concentration, and the relationship is approximated as a linearly decreasing function. FIG. 5a is similar to FIG. 4a, and FIG. 5b is similar to FIG. 4b, except for the different glucose concentration. Note that the glucose concentration around 20 mg/dl can be measured in FIG. 5a and FIG. 5b.

In some embodiments, the controlling module 150 may substitute the parameter γ into a linearly increasing function to calculate the glucose concentration, or substitute the parameter Δ into a linearly decreasing function to calculate the glucose concentration. The linearly increasing function or the linearly decreasing function may be represented as y=ax+b where y is the glucose concentration, x is the parameter γ or Δ, and a and b are constants. However, the invention is not limited thereto. In other embodiments, the parameter γ, Δ, or the combination thereof may be taken as input, and the known glucose concentration is taken as output for performing a regression analysis to obtain constants in a mathematic model. The mathematic model may be a linear function (applied in the embodiment), a polynomial function, an exponential function, or other functions. Moreover, how many constants exist in the mathematic model is not limited in the invention. For example, if the polynomial function is applied, the model may be expressed as $y=ax^2+bx+c$ where a, b, and c are constants, and x is the parameter γ or Δ. The person in the art should be able to understand the regression analysis and figure out another mathematic model. Alternatively, the parameter γ, Δ, or the combination thereof may be taken as input, the known glucose concentration is taken as output to train a machine learning model such as neural network, support vector machine, etc. In some embodiments, the parameter γ, Δ, or the combination thereof may be just a portion of the input.

In the aforementioned embodiments, the differential Mueller matrix is used to calculate the parameters γ and Δ, but in other embodiments, the parameters γ and Δ may be calculated by decomposing the Mueller matrix, which is not limited in the invention. For example, another algorithm for calculating the parameters γ and Δ are disclosed by the thesis "Extraction of effective parameters of turbid media utilizing Mueller matrix approach: study of glucose sensing", Journal of Biomedical Optics 17(9), 097002 (2012) written by Thi-Thu-Hien Pham and Yu-Lung Lo and this algorithm may also be applied in the sensing system of the present application. On the other hand, the Stokes vectors are calculated by the polarization state analyzer 140 by using Fourier transform in the aforementioned embodiment, but in other embodiments, the Stokes vector may be calculated by adopting other suitable device and/or algorithms, which is not limited in the invention.

In the embodiments, the glucose concentration can be calculated in one period (e.g. 1/80 k seconds) of the electrical signal. Therefore, the measurement is done very quickly that can avoid external interference and thus increase the measurement accuracy. In some embodiments, one glucose concentration is calculated in each period, and the average of the glucose concentrations in a short time (e.g. one second) is calculated. However, the person in the art should be able to adjust the parameters such as period, time, etc., which is not limited in the invention. Alternatively, some signal processing approaches such as noise removing, extreme value removing may be performed on the obtained glucose concentrations. The content of the signal processing is not limited in the invention.

Figure 6:
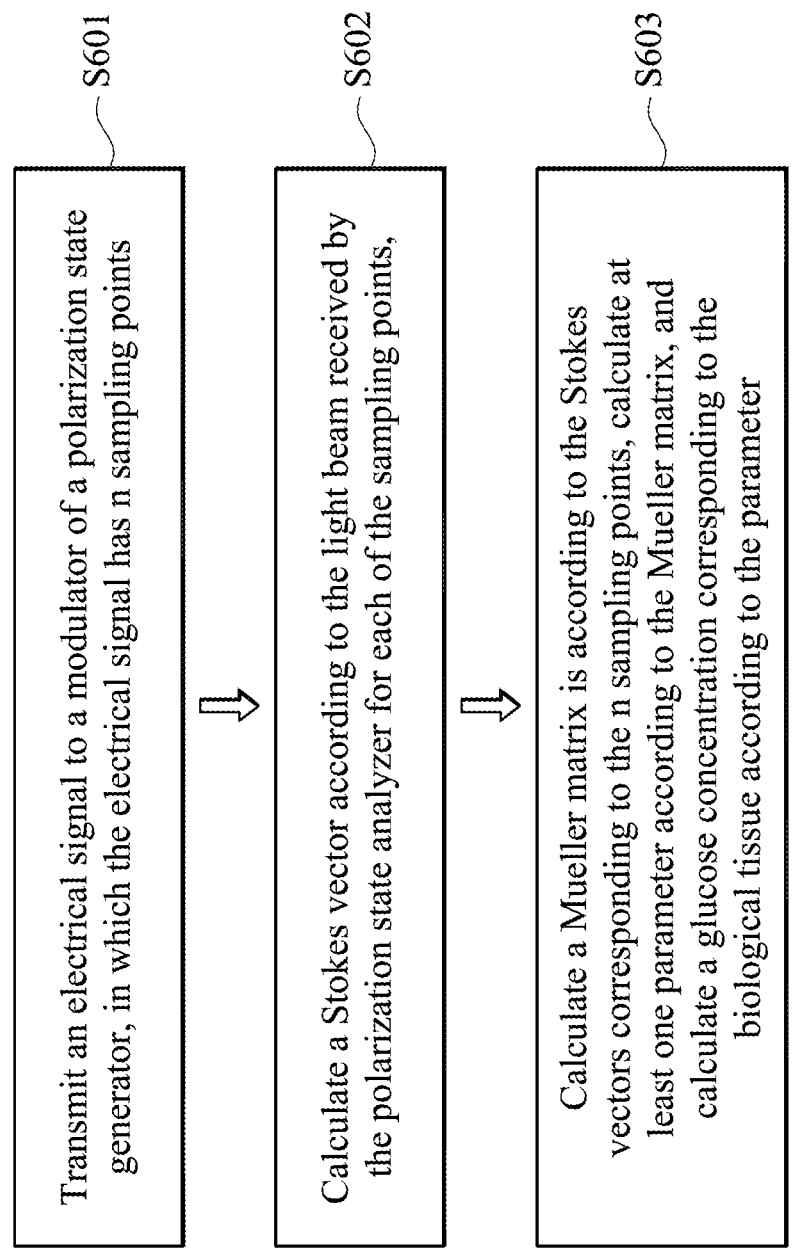
FIG. 6 is a diagram illustrating a flow chart of the method for sensing the glucose concentration in accordance with an embodiment.

FIG. 6 is a diagram illustrating a flow chart of the method for sensing the glucose concentration in accordance with an embodiment. The method may be applied to the embodiments of FIG. 1, FIG. 2 or FIG. 3. In step S601, an electrical signal is transmitted to a modulator of a polarization state generator, in which the electrical signal has n sampling points. In step S602, for each of the sampling points, a Stokes vector is calculated according to the light beam received by the polarization state analyzer. In step S603, a Mueller matrix is calculated according to the Stokes vectors corresponding to the n sampling points, at least one parameter is calculated according to the Mueller matrix, and a glucose concentration corresponding to the biological tissue is calculated according to the parameter. However, all the steps in FIG. 6 have been described in detail above, and therefore they will not be repeated. Note that the steps in FIG. 6 can be implemented as program codes or circuits, and the disclosure is not limited thereto. In addition, the method in FIG. 6 can be performed with the aforementioned embodiments, or can be performed independently. In other words, other steps may be inserted between the steps of the FIG. 6.

In the system and method provided in the embodiments of the invention, the glucose concentration as low as 20 mg/dl can be measured. In addition, the sensing system could be noninvasive that only needs to emit the light beam to a human finger, and thus the glucose measurement is very simple and convenient.

Figure 7:
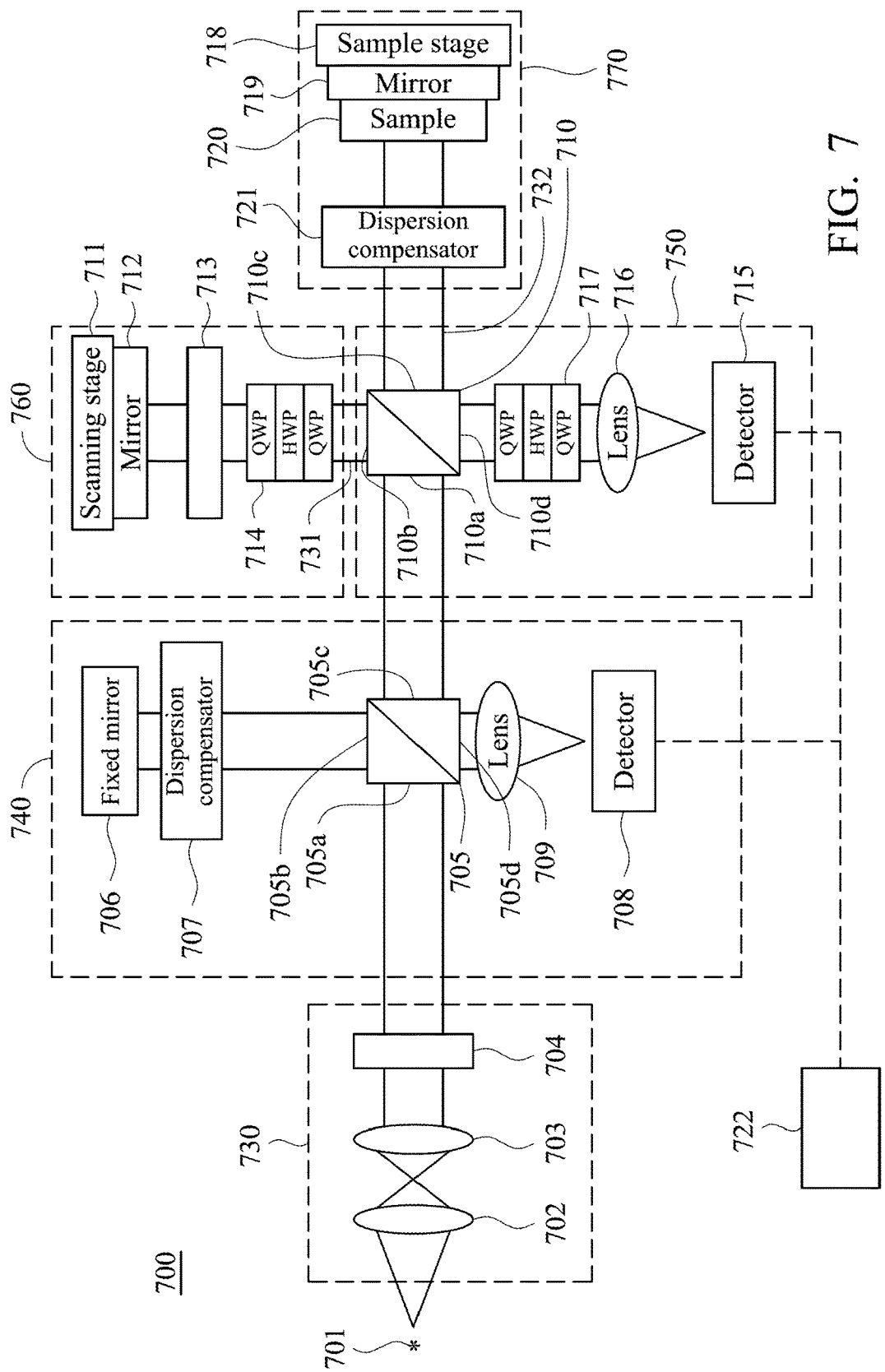
FIG. 7 is a schematic diagram illustrating a system for sensing glucose concentration in accordance with some embodiments.

FIG. 7 is a schematic diagram illustrating a system 700 for sensing glucose concentration in accordance with some embodiments. Referring to FIG. 7, the system 700 includes a light source 701 and an optical coherence tomography (OCT) device. The light source 701 (e.g. a thermal light source is adopted to enhance the axial resolution) is configured to generate a light beam. The OCT device includes a polarization state generator 730 for receiving the light beam and change the polarization of the light beam; a first detecting module 740 for compensating and splitting the light beam; a second detecting module 750 coupled to the first detecting module for splitting the light beam again; a reference arm 760 disposed at a side of the second detecting module 750; a measurement arm 770 disposed at another side of the second detecting module 750.

In detail, the light beam passes through the lens 702 and 703, and then is emitted to a combined polarizer and quarter-wave plate 704. A first non-polarizing beam splitter (NPBS) 705 has a first side 705a, a second side 705b, a third side 705c and a fourth side 705d. The first side 705a is opposite to the third side 705c, and the second side 705b is opposite to the fourth side 705d. The polarizer and quarter-wave plate 704 is disposed at the first side 705a of the first NPBS 705. A fixed mirror 706 is disposed at the second side 705b. A dispersion compensator 707 is disposed between the mirror 706 and the first NPBS 705. A detector 708 is disposed at the fourth side 705d of the first NPBS 705. A lens 709 is disposed between the detector 708 and the first NPBS 705. A second NPBS 710 is disposed at the third side 705c of the first NPBS 705. The NPBS 710 has a first side 710a, a second side 710b, a third side 710c and a fourth side 710d, in which the first side 710a is opposite to the third side 710c, and the second side 710b is opposite to the fourth side 710d.

detector 715. In detail, the signal received by the detector 708 is used for calibration, and the signal received by the detector 715 is used to obtain the intensity of the light beam. The process for the calibration and for obtaining the intensity is referred to "Measurement of Multiple Optical Parameters of Birefringent Sample Using Polarization-Sensitive Optical Coherence Tomography," by C.-C. Liao, Y.-L. Lo, and C.-Y. Yeh, *Journal of Lightwave Technology*, vol. 27, pp. 483-493, 2009, which is incorporated by reference.

To calculate the Mueller matrix of the sample 720, the quarter-wave plate and polarizer 704 are rotated to obtain four different polarization states of the light beam incident on the sample 720, namely H (horizontal linear polarization), V (vertical linear polarization), P (45° linear polarization), and R (right-circular polarization). In addition, the variable wave plate 713 is adjusted to change the polarization state of the reference beam 731 sequentially to H, V, P, and R, respectively, for each of the four incident lights. Thus, a total of 16 interferometric signals are produced with which to investigate the sample 720 and detected by the detector 715. The 16 elements in the 4×4 Mueller matrix are then computed as the following equation (30).

$$M = \begin{bmatrix} M_{11} & M_{12} & M_{13} & M_{14} \\ M_{21} & M_{22} & M_{23} & M_{24} \\ M_{31} & M_{32} & M_{33} & M_{34} \\ M_{41} & M_{42} & M_{43} & M_{44} \end{bmatrix}$$

$$= \begin{bmatrix} HH+HV+VH+VV & HH+HV-VH-VV & 2PH+2PV-M_{11} & 2RH+2RV-M_{11} \\ HH-HV+VH-VV & HH-HV-VH+VV & 2PH-2PV-M_{21} & 2RH-2RV-M_{21} \\ 2HP+2VP-M_{11} & 2HP-2VP-M_{12} & 4PP-2PH-2PV-M_{31} & 4RP-2RH-2RV-M_{31} \\ 2HR+2VR-M_{11} & 2HR-2VR-M_{12} & 4PR-2PH-2PV-M_{41} & 4RR-2RH-2RV-M_{41} \end{bmatrix}$$

(30)

A scanning stage 711 is disposed at the second side 710b. A mirror 712 is disposed between the scanning stage 711 and the NPBS 710. A variable wave plate 713 is disposed between the mirror 712 and the NPBS 710. A compensator 714 is disposed between the variable wave plate 713 and the NPBS 710. The compensator 714 includes two quarter-wave plates and one half-wave plate. A detector 715 is disposed at the fourth side 710d. A lens 716 is disposed between the detector 715 and the NPBS 710. A compensator 717 is disposed between the lens 716 and the NPBS 710. The compensator 717 includes two quarter-wave plates and one half-wave plate. A sample stage 718 is disposed at the third side 710c. A mirror 719 is disposed between the sample stage 718 and the NPBS 710. A sample 720 is disposed between the mirror 719 and the NPBS 710. A dispersion compensator 721 is disposed between the sample 720 and the NPBS 710. A controlling module 722 is coupled to the detectors 708 and 715.

The light beam from the light source 701 is split by the NPBS 705 into two beams, where one beam is incident upon the fixed mirror 706 while the other light beam passes through the NPBS 710 and is again split into two beams, namely a reference beam 731 and a measurement beam 732. The reference beam 731 passes through the variable wave plate 713 designed to control the polarization state and is then reflected by the mirror 712 mounted on the scanning stage 711 used to carry out path-length scanning. Meanwhile, the measurement beam 732 passes through dispersion compensator 721 used to compensate for the dispersion effect and is then incident upon the sample 720.

The controlling module 722 calculates a Muller matrix according to signals received by the detector 708 and the $M_{ij}$ is the Mueller matrix element of the $i^{th}$ row and $j^{th}$ column. The left and right symbols in each double polarization state notation represent the polarization states of the measurement light beam 732 and the reference light beam 731, respectively. For example, the notation HV refers to the interferometric signal obtained given a horizontal linear polarized measurement light beam and a vertical linear polarized reference light beam.

The controlling module 722 also calculates the optical rotation angle γ and the depolarization index Δ according to the Muller matrix obtained by the equation (30). To be specific, the measurement light beam 732 passes through the sample 720 in both the forward direction and the backward direction. As shown in FIG. 7, the measurement light beam 732 is transmitted through the NPBS 710, forward through the sample 720, reflected from the mirror 719, transmitted backward through the sample 720, and finally reflected from the NPBS 710 such that it is incident on the detector 715. Accordingly, the optical arrangement shown in FIG. 7 can be modeled using the following Mueller matrix representation.

$$M_{CB/Dep,OCT} = M_{R,BS} M_{CB/Dep} M_{Mirror} M_{CB/Dep} M_{T,BS} \tag{31}$$

$M_{Mirror}$ is the Mueller matrix of the mirror 719. $M_{T,BS}$ and $M_{R,BS}$ are the Mueller matrixes of the NPBS 710 in the transmission mode and reflection mode, respectively. $M_{CB/Dep}$ is the Mueller matrixes containing CB and depolarization properties. General forms of all the Mueller matrices describing the optical components in the equation (31) are shown as the following equations (32)-(34).

$$M_{Mirror} = \begin{bmatrix} 1 & 0 & 0 & 0 \\ 0 & 1 & 0 & 0 \\ 0 & 0 & -1 & 0 \\ 0 & 0 & 0 & -1 \end{bmatrix} \quad (32)$$

$$M_{R,BS} = \begin{bmatrix} 1 & 0 & 0 & 0 \\ 0 & 1 & 0 & 0 \\ 0 & 0 & -1 & 0 \\ 0 & 0 & 0 & -1 \end{bmatrix} \quad (33)$$

$$M_{T,BS} = \begin{bmatrix} 1 & 0 & 0 & 0 \\ 0 & 1 & 0 & 0 \\ 0 & 0 & 1 & 0 \\ 0 & 0 & 0 & 1 \end{bmatrix} \quad (34)$$

Thus, the Mueller matrix of a CB/Dep sample describing the circular birefringence with the scattering effect can be expressed as the following equations (35) and (36).

$$M_{CB/Dep} = M_{CB} M_\Delta \quad (35)$$

$$M_{CB} = \begin{bmatrix} 1 & 0 & 0 & 0 \\ 0 & \cos(2\gamma) & \sin(2\gamma) & 0 \\ 0 & -\sin(2\gamma) & \cos(2\gamma) & 0 \\ 0 & 0 & 0 & 1 \end{bmatrix} \quad (36)$$

$\gamma$ is the optical rotation angle. It is noted that the differential Mueller matrix of scattering effect can be expressed as the following equation (37).

$$m_\Delta = \begin{bmatrix} 0 & 0 & 0 & 0 \\ 0 & -d_1 & \eta_v & 0 \\ 0 & \eta_v & -d_2 & 0 \\ 0 & 0 & 0 & -d_3 \end{bmatrix} \quad (37)$$

$d_{1-3}$ are the anisotropic absorptions coefficients along the x-y, 45°, and circular axes. The $\eta_v$ parameter is the mean value of the nondepolarizing property. Performing an inverse differential calculation, the macroscopic Mueller matrix describing the scattering effect, $M_\Delta$, can be expressed as the following equation (38).

$$M_\Delta = \begin{bmatrix} 1 & 0 & 0 & 0 \\ 0 & K_{22} & K_{23} & 0 \\ 0 & K_{32} & K_{33} & 0 \\ 0 & 0 & 0 & K_{44} \end{bmatrix} \quad (38)$$

The variables in the equations (36) and (38) are obtained by equating the Muller matrix of the equation (31) to that of the equation (30). For example, a genetic algorithm may be adopted to search the variables, but the invention is not limited thereto. Then, the depolarization index $\Delta$ can be calculated as the following equation (39).

$$\Delta = \sqrt{\frac{K_{22}^2 + K_{33}^2 + K_{44}^2}{3}} \quad (39)$$

Then, the controlling module 722 calculates a glucose concentration corresponding to the sample according to the optical rotation angle and the depolarization index.

Figure 8:
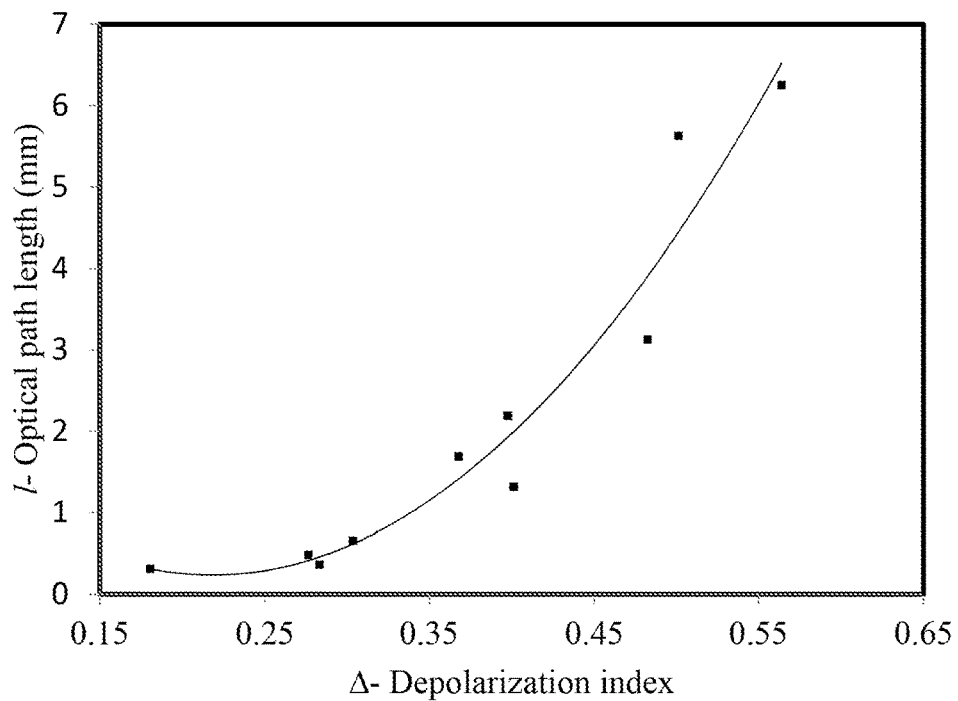
FIG. 8 is a diagram illustrating relationship between the depolarization index and the optical path length.

FIG. 8 is a diagram illustrating relationship between the depolarization index and the optical path length. First, an optical path length is obtained in accordance with the depolarization index. Referring to FIG. 8, The Rayleigh model describes scattering of light by particles whose size is much smaller than the wavelength of the light. For arbitrary values of the mean free path (l) and the length of the sample (L), some rays (i.e. light beams) may pass through the sample without undergoing bulk scattering. The fraction of "unscattered" rays (or the depolarization index) can be determined from the fact that rays which travel a distance x within the sample have an integrated probability of having been scattered given by the following equation (40).

$$p(x) = 1.0 - e^{-x/l} \quad (40)$$

Thus, the integrated probability of a ray travelling a distance x within the sample and not undergoing scattering is given by the following equation (41).

$$1 - p(x) = e^{-x/l} \quad (41)$$

Setting x=L, we find that the probability of a ray traveling through the full sample and not being scattered is as the following equation (42). That is, the optical path length (l) is obtained by substituting the depolarization index into the equation (42).

$$\Delta = e^{-L/l} \quad (42)$$

Figure 9:
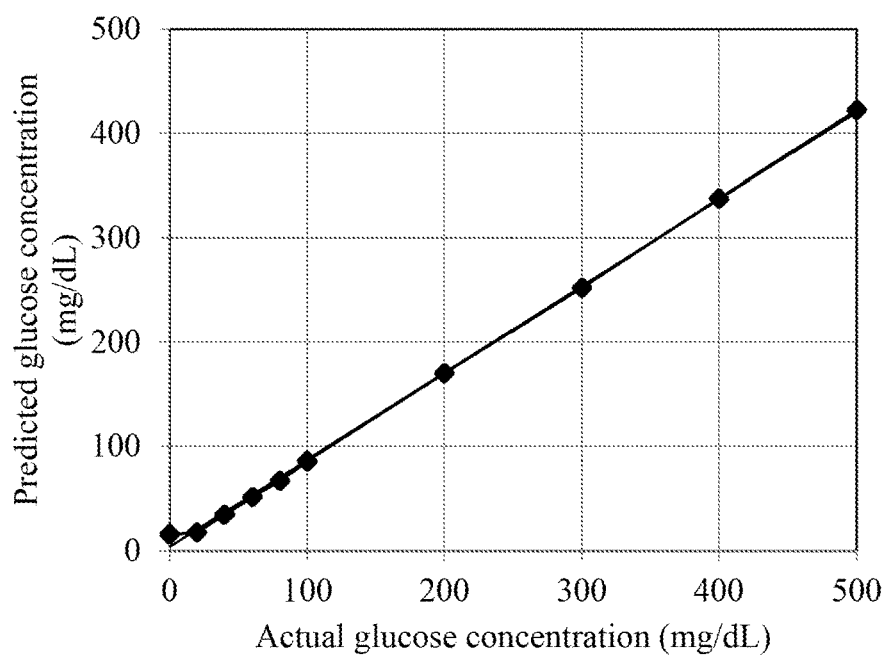
FIG. 9 is a diagram illustrating relationship between the predicted glucose concentration and the actual glucose concentration.

The extracted values of glucose concentration are obtained by the following equation (43).

$$C = \frac{\gamma}{[\gamma]_T^\lambda l} \quad (43)$$

where $\gamma$ is the experimental value of the optical rotation angle. l is the optical path length obtained from the equation (40). $[\gamma]_T^\lambda$ is the optical rotation angle of the sample at room temperature T and wavelength $\lambda$ of the light beam obtained from "New optical scheme for a polarimetric based glucose sensor" by R. R. Ansari, S. Bockle and L. Rovati, J. Biomed. Opt. 9, pp. 103-115 (2204). Referring to FIG. 9, the predicted glucose concentration is close to the actual glucose concentration. Note that the equations (40)-(43) may be applied to the embodiments of FIG. 1 to FIG. 6.

Although the present invention has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A system for sensing glucose concentration, the system comprising:
a light source configured to generate a light beam;
a polarization state generator configured to receive the light beam, wherein the polarization state generator comprises a modulator for changing a polarization of the light beam, and the light beam passing the modulator is emitted to a biological tissue;

a polarization state analyzer configured to receive the light beam reflected from the biological tissue; and a controlling module configured to transmit an electrical signal to the modulator, wherein the electrical signal has n sampling points which correspond to n polarizations of the light beam respectively, the n polarizations are different from each other, and n is a positive integer greater than or equal to 4, wherein for each of the n sampling points, the controlling module calculates a Stokes vector according to the light beam received by the polarization state analyzer, wherein the controlling module calculates a Mueller matrix according to the Stokes vectors corresponding to the n sampling points, and calculates at least one parameter according to the Mueller matrix, wherein the at least one parameter comprises a depolarization index or an optical rotation angle, wherein the controlling module calculates a glucose concentration corresponding to the biological tissue according to the at least one parameter.

2. The system of claim 1, wherein the polarization state generator further comprises:

a polarizer disposed between the modulator and the light source, wherein a principal axis of the polarizer is 0°; and a quarter-wave plate disposed between the modulator and the biological tissue, wherein a principal axis of the quarter-wave plate is 0°, wherein a principal axis of the modulator is 45°.

3. The system of claim 1, wherein the polarization state generator further comprises:

a polarizer disposed between the modulator and the light source;

a quarter-wave plate disposed between the modulator and the biological tissue; and a half-wave plate disposed between the quarter-wave plate and the biological tissue.

4. The system of claim 3, wherein the modulator is an electro-optic modulator, a principal axis of the polarizer is 0°, a principal axis of the electro-optic modulator is 45°, a principal axis of the quarter-wave plate is 45°, and a principal axis of the half-wave plate is 45°, wherein a Stokes vector of the light beam emitted by the polarization state generator is represented by following equations (1) and (2):

$$S' = \begin{bmatrix} 1 \\ \cos a \\ \sin a \\ 1 \end{bmatrix} \quad (1)$$

$$a = \frac{\pi V}{V_{\lambda/2}} \quad (2)$$

wherein S' is the Stokes vector of the light beam emitted by the polarization state generator, V is a constant, $V_{\lambda/2}$ is an amplitude of the electrical signal.

5. The system of claim 4, wherein the polarization state analyzer comprises:

a second electro-optic modulator with a principal axis of 0°;

a third electro-optic modulator with a principal axis of 45°, wherein the second electro-optic modulator is disposed between the biological tissue and the third electro-optic modulator;

an analyzer with a principal axis of 0°; and a detector, wherein the analyzer is disposed between the third electro-optic modulator and the detector, and the detector is configured to receive the light beam passing through the second electro-optic modulator, the third electro-optic modulator, and the analyzer.

6. The system of claim 5, wherein the controlling module performs a Fourier transform on brightness of the light beam received by the detector to obtain a plurality of brightness parameters, and calculates a plurality of Stokes parameters of the corresponding Stokes vector according to the plurality of brightness parameters.

7. The system of claim 6, wherein the controlling module calculates a differential Mueller matrix according to following equations (3) and (4):

$$\lambda_m = \ln(\lambda_M)/z \quad (3)$$

$$m = V_M m_\lambda V_M^{-1} = \begin{bmatrix} m_{11} & m_{12} & m_{13} & m_{14} \\ m_{21} & m_{22} & m_{23} & m_{24} \\ m_{31} & m_{32} & m_{33} & m_{34} \\ m_{41} & m_{42} & m_{43} & m_{44} \end{bmatrix} \quad (4)$$

wherein z represents a direction that the light beam propagates along, m is the differential Mueller matrix, $V_M$ represents eigenvectors of the Mueller matrix, $\lambda_M$ represents eigenvalues of the Mueller matrix, $\lambda_m$ represents eigenvalues of the differential Mueller matrix, $m_\lambda$ is a diagonal matrix constituted by the eigenvalues $\lambda_m$, and the optical rotation angle is represented as $\gamma = (m_{23} - m_{32})/4$.

8. The system of claim 7, wherein the controlling module generates a differential Mueller matrix $m_\Delta$ as a following equation (5) according to the differential Mueller matrix m:

$$m_\Delta = \begin{bmatrix} 0 & \frac{(m_{12}-m_{21})}{2} & \frac{(m_{13}-m_{31})}{2} & \frac{(m_{14}-m_{41})}{2} \\ \frac{(m_{21}-m_{12})}{2} & m_{22}-m_{11} & \frac{(m_{23}+m_{32})}{2} & \frac{(m_{24}+m_{42})}{2} \\ \frac{(m_{31}-m_{13})}{2} & \frac{(m_{23}+m_{32})}{2} & m_{33}-m_{11} & \frac{(m_{34}+m_{43})}{2} \\ \frac{(m_{41}-m_{14})}{2} & \frac{(m_{24}+m_{42})}{2} & \frac{(m_{34}+m_{43})}{2} & m_{44}-m_{11} \end{bmatrix} \quad (5)$$

the controlling module substitutes the differential Mueller matrix $m_\Delta$ into the equation (4) to calculate a Mueller matrix $M_\Delta$ as a following equation (6):

$$M_\Delta = \begin{bmatrix} 1 & K_{12} & K_{13} & K_{14} \\ -K_{12} & K_{22} & K_{23} & K_{24} \\ -K_{13} & K_{23} & K_{33} & K_{34} \\ -K_{14} & K_{24} & K_{34} & K_{44} \end{bmatrix} \quad (6)$$

wherein the depolarization index is represented as a following equation (7):

$$\Delta = 1 - \sqrt{\frac{K_{22}^2 + K_{33}^2 + K_{44}^2}{3}}. \quad (7)$$

9. The system of claim 8, wherein the controlling module substitutes the optical rotation angle into a linearly increasing function to obtain the glucose concentration, or substitutes the depolarization index into a linearly decreasing function to obtain the glucose concentration.

10. The system of claim 8, wherein the controlling module obtains an optical path length in accordance with a following equation (8):

$$\Delta = e^{-L/l} \quad (8)$$

wherein Δ is the depolarization index, L is a length of the sample, and l is the optical path length,
wherein the controlling module calculates the glucose concentration corresponding to the sample in accordance with a following equation (9):

$$C = \frac{\gamma}{[\gamma]_T^\lambda l} \quad (9)$$

where C is the glucose concentration, γ is the optical rotation angle, $[\gamma]_T^\lambda$ is the optical rotation angle of the sample at room temperature T, and λ is a wavelength of the light beam.

11. A method for sensing glucose concentration for a system which comprises a light source, a polarization state generator and a polarization state analyzer, wherein a light beam generated by the light source is emitted to the polarization state generator and then is emitted to a biological tissue, the polarization state analyzer receives the light beam reflected from the biological tissue, and the method comprises:
    transmitting an electrical signal to a modulator of the polarization state generator, wherein the electrical signal has n sampling points which correspond to n polarizations of the light beam respectively, the n polarizations are different from each other, and n is a positive integer greater than or equal to 4;
    calculating a Stokes vector according to the light beam received by the polarization state analyzer for each of the n sampling points; and
    calculating a Mueller matrix according to the Stokes vectors corresponding to the n sampling points, calculating at least one parameter according to the Mueller matrix, and calculating a glucose concentration corresponding to the biological tissue according to the at least one parameter, wherein the at least one parameter comprises a depolarization index or an optical rotation angle.

12. A system for sensing glucose concentration, the system comprising:
    a light source configured to generate a light beam;
    an optical coherence tomography (OCT) device configured to receive the light beam, wherein the optical coherence tomography comprises at least one detector; and
    a controlling module, calculating a Muller matrix according to signals received by the at least one detector, and calculating an optical rotation angle and a depolarization index according to the Muller matrix, and calculating a glucose concentration corresponding to a sample according to the optical rotation angle and the depolarization index.

13. The system of claim 12, wherein the optical coherence tomography device comprises:
    a polarization state generator, configured to receive the light beam and change a polarization of the light beam;
    a first detecting module, configured to compensate the light beam and split the light beam;
    a second detecting module, coupled to the first detecting module and configured to split the light beam;
    a reference arm, disposed at a side of the second detecting module; and
    a measurement arm, disposed at another side of the second detecting module.

14. The system of claim 13,
    wherein the polarization stage generator comprises:
        a polarizer and a quarter-wave plate, configured to receive light; and
        a plurality of first lens disposed between the light source and the polarizer and the quarter-wave plate,
    wherein the first detecting module comprises:
        a first non-polarizing beam splitter (NPBS) having a first side, a second side, a third side and a fourth side, wherein the first side is opposite to the third side, the second side is opposite to the fourth side, and the polarizer and the quarter-wave plater are disposed at the first side of the first NPBS;
        a first mirror, disposed at the second side of the first NPBS;
        a first dispersion compensator disposed between the first mirror and the first NPBS;
        a first detector, disposed at the fourth side of the first NPBS;
        a second lens disposed between the first NPBS and the first detector,
    wherein the second detecting module comprises:
        a second NPBS, disposed at the third side of the first NPBS and having a first side, a second side, a third side and a fourth side, wherein the first side of the second NPBS is opposite to the third side of the second NPBS, the second side of the second NPBS is opposite to the fourth side of the second NPBS;
        a second detector, disposed at the fourth side of the second NPBS;
        a third lens, disposed between the second NPBS and the second detector; and
        a first compensator, disposed between the second NPBS and the third lens,
    wherein the reference arm comprises:
        a scanning stage, disposed at the second side of the second NPBS;
        a second mirror, disposed between the scanning stage and the second NPBS;
        a variable wave plater, disposed between the second mirror and the second NPBS; and
        a second compensator, disposed between the second NPBS and the variable wave plater,
    wherein the measurement arm comprises:
        a sample stage, disposed at the third side of the second NPBS;
        a third mirror, disposed between the second NPBS and the sample stage;
        the sample, disposed between the third mirror and the second NPBS; and
        a second dispersion compensator, disposed between the second NPBS and the sample.

15. The system of claim 14, wherein the first compensator comprises two quarter-wave plates and one half-wave plate, wherein the second compensator comprises two quarter-wave plates and one half-wave plate.

16. The system of claim 15, wherein the controlling module rotates the quarter-wave plate and the polarizer, and adjusts the variable wave plate to produce at least 16 interferometric signals detected by the second detector,
wherein the controlling module calculates the Muller matrix according to the 16 interferometric signals.

17. The system of claim 16, wherein the controlling module obtains an optical path length in accordance with a following equation (1):

$$\Delta = e^{-L/l} \qquad (1)$$

wherein $\Delta$ is the depolarization index, L is a length of the sample, and l is the optical path length,
wherein the controlling module calculates the glucose concentration corresponding to the sample in accordance with a following equation (2):

$$C = \frac{\gamma}{[\gamma]_T^\lambda l} \qquad (2)$$

where C is the glucose concentration, $\gamma$ is the optical rotation angle, $[\gamma]_T^\lambda$ is the optical rotation angle of the sample at room temperature T, and $\lambda$ is a wavelength of the light beam.

* * * * *